(12) United States Patent
Higano

(10) Patent No.: US 11,535,523 B2
(45) Date of Patent: *Dec. 27, 2022

(54) METHOD FOR PRODUCING METAL OXIDE DISPERSION LIQUID AND METHOD FOR PRODUCING INFRARED-RADIATION-SHIELDING FILM

(71) Applicant: MITSUBISHI MATERIALS CORPORATION, Tokyo (JP)

(72) Inventor: Satoko Higano, Naka (JP)

(73) Assignee: MITSUBISHI MATERIALS CORPORATION, Tokyo (JP)

( * ) Notice: Subject to any disclaimer, the term of this patent is extended or adjusted under 35 U.S.C. 154(b) by 235 days.

This patent is subject to a terminal disclaimer.

(21) Appl. No.: 16/770,964

(22) PCT Filed: Feb. 7, 2019

(86) PCT No.: PCT/JP2019/004426
§ 371 (c)(1),
(2) Date: Jun. 9, 2020

(87) PCT Pub. No.: WO2019/159805
PCT Pub. Date: Aug. 22, 2019

(65) Prior Publication Data
US 2021/0179440 A1  Jun. 17, 2021

(30) Foreign Application Priority Data
Feb. 14, 2018 (JP) .............................. JP2018-023647

(51) Int. Cl.
*C01G 19/02* (2006.01)
*C01G 9/02* (2006.01)
*C01G 30/00* (2006.01)
*G02B 5/22* (2006.01)

(52) U.S. Cl.
CPC ............... *C01G 19/02* (2013.01); *C01G 9/02* (2013.01); *C01G 30/005* (2013.01); *G02B 5/22* (2013.01)

(58) Field of Classification Search
CPC .................................................... C01G 19/02
See application file for complete search history.

(56) References Cited

U.S. PATENT DOCUMENTS

| 5,993,861 A | 11/1999 | Fogel |
| 2004/0192951 A1 | 9/2004 | Sawada et al. |
| 2006/0211152 A1 | 9/2006 | Peng et al. |
| 2015/0160379 A1 | 6/2015 | Shen et al. |
| 2015/0291501 A1 | 10/2015 | Yang et al. |
| 2016/0317992 A1 | 11/2016 | Thuo et al. |

FOREIGN PATENT DOCUMENTS

| CN | 1872917 A | 12/2006 |
| CN | 101962516 A | 2/2011 |
| CN | 102251285 A | 11/2011 |
| CN | 102470090 A | 5/2012 |
| CN | 102498169 A | 6/2012 |
| CN | 102791870 A | 11/2012 |
| CN | 104725900 A | 6/2015 |
| CN | 107162044 A | 9/2017 |
| EP | 3578515 A1 | 12/2019 |
| JP | H05-070717 A | 3/1993 |
| JP | H07-109119 A | 4/1995 |
| JP | H08-041441 A | 2/1996 |
| JP | 10-265718 A | 10/1998 |
| JP | 2002-015631 A | 1/2002 |
| JP | 2004-300539 A | 10/2004 |
| JP | 2005-154654 A | 6/2005 |
| JP | 2007-145712 A | 6/2007 |
| JP | 2008-074911 A | 4/2008 |
| JP | 2008-521591 A | 6/2008 |
| JP | 2008-266050 A | 11/2008 |
| JP | 2008-297414 A | 12/2008 |
| JP | 2010-240520 A | 10/2010 |
| JP | 2012-176859 A | 9/2012 |
| JP | 2013-001954 A | 1/2013 |
| JP | 2013-089533 A | 5/2013 |
| JP | 2013-216858 A | 10/2013 |
| JP | 2014-145050 A | 8/2014 |
| JP | 2015-003940 A | 1/2015 |

(Continued)

OTHER PUBLICATIONS

Boubbou, Journal of Nanomaterials (2015) 620672/1-620672/12. 1687-4129.*
Supplementary European Search Report dated Oct. 20, 2021, issued for European Patent Application No. 19753901.8.
Shaojuan Luo, et al., "Synthesis and application of non-agglomerated ITO nanocrystals via pyrolysis of indium-tin stearate without using additional organic solvents", Journal of Nanoparticle Research, vol. 16(8), 2014, 2561, pp. 1 to 12.
International Search Report dated Mar. 6, 2018, issued for PCT/JP2018/002448 and English translation thereof.
Shaojuan Luo et al., "Effect of fatty acid on the formation of ITO nanocrystals via one-pot pyrolysis reaction", CrystEngComm, vol. 17, No. 5, 2015, pp. 1168-1172.

(Continued)

*Primary Examiner* — Nizal S Chandrakumar
(74) *Attorney, Agent, or Firm* — Locke Lord LLP

(57) ABSTRACT

According to this method, a fatty acid of $CnH_{2n}O_2$ (n=5 to 14) is mixed with a plurality of metal sources selected from Zn, In, Sn, Sb, and Al, thereby fatty acid metal salts are obtained, subsequently the fatty acid metal salts are heated at 130° C. to 250° C., and a metal soap that is a precursor is obtained. This precursor is heated at 200° C. to 350° C., and metal oxide primary particles are dispersed in the precursor melt. To this dispersion liquid, a washing solvent having a δP value higher by 5 to 12 than the δP value of the Hansen solubility parameter of the final dispersing solvent is added, thereby the metal oxide primary particles are washed and agglomerated, metal oxide secondary particles are obtained, and then washing is repeated.

8 Claims, 1 Drawing Sheet

(56) References Cited

FOREIGN PATENT DOCUMENTS

| | | | |
|---|---|---|---|
| JP | 2015-003941 A | 1/2015 |
| JP | 2015-511575 A | 4/2015 |
| JP | 2016-118679 A | 6/2016 |
| JP | 2017-024932 A | 2/2017 |
| TW | 201336786 A | 9/2013 |
| WO | 2006/057467 A1 | 6/2006 |
| WO | 2006/098756 A2 | 9/2006 |
| WO | 2017/217459 A1 | 12/2017 |
| WO | 2018/143076 A1 | 8/2018 |

OTHER PUBLICATIONS

Notice of Allowance dated Jul. 7, 2020, issued for Japanese Patent Application No. 2017-019315 and English translation thereof.
Supplementary European Search Report dated Nov. 23, 2020, issued for European Patent Application No. 18747384.8.
Office Action dated Dec. 29, 2020, issued for Taiwanese Patent Application No. 107103555 and English translation thereof.
Notice of Allowance dated Apr. 12, 2021, issued for Korean Patent Application No. 10-2019-7019650 and English translation thereof.
International Search Report dated Jun. 18, 2019, issued for PCT/JP2019/011114 and English translation thereof.
Office Action dated Oct. 21, 2021, issued for U.S. Appl. No. 16/482,804.
Shaojuan Luo et al., "Synthesis and application of non-agglomerated ITO nanocrystals via pyrolysis of indium-tin stearate without using additional organic solvents," J Nanopart Res vol. 16(8) 2014, 2561 pp. 1-12. (discussed in the spec).
International Search Report dated Mar. 19, 2019, issued for PCT/JP2019/004426 and English translation thereof.
Matsui Hiroaki et al., "Infrared Solar Thermal-Shielding Applications Based on Oxide Semiconductor Plasmonics", Nanoplasmonics—Fundamentals and Applications, Chapter 8, IntechOpen, Jun. 21, 2017, pp. 173-193 and cover page.
Supplementary European Search Report dated Nov. 26, 2021, issued for European Patent Application No. 19770894.4.
Office Action dated Nov. 2, 2021, issued for Japanese Patent Application No. 2018-053819 and English translation thereof.
Qianqian Dou et al., "Synthesis of various metal stearates and the corresponding monodisperse metal oxide nanoparticles" Powder Technology, 2016, pp. 949-958.
Office Action issued in corresponding Chinese Patent Application No. CN 201980007579.5, dated Mar. 1, 2022.
Office Action issued in corresponding Taiwanese Patent Application No. TW 108109506, dated Mar. 31, 2022.
Office Action dated Mar. 2, 2022, issued for U.S. Appl. No. 16/771,831.
Notice of Allowance dated Jul. 20, 2021, issued for Japanese Patent Application No. 2018-023647 and English translation thereof.

* cited by examiner

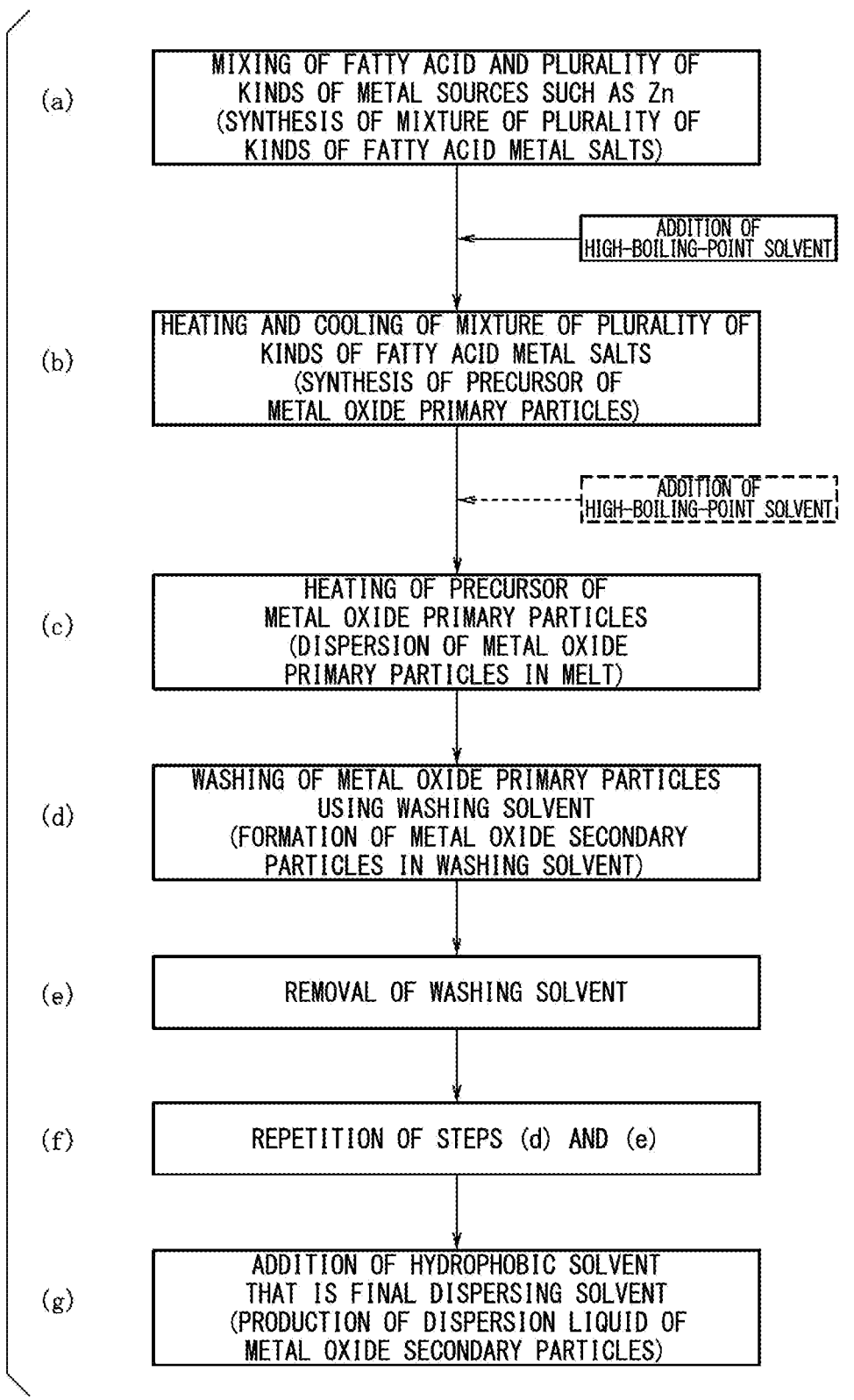

METHOD FOR PRODUCING METAL OXIDE DISPERSION LIQUID AND METHOD FOR PRODUCING INFRARED-RADIATION-SHIELDING FILM

TECHNICAL FIELD

The present invention relates to a method for producing a dispersion liquid of a metal oxide using a fatty acid, a plurality of kinds of metals, and the like as starting raw materials, and a method for producing an infrared-radiation-shielding film using the dispersion liquid.

Priority is claimed on Japanese Patent Application No. 2018-023647 filed on Feb. 14, 2018, the content of which is incorporated herein by reference.

BACKGROUND ART

For example, Non-Patent Literature 1 discloses a method of directly reacting stearic acid, which is a kind of fatty acid, with metal indium and metal tin at 260° C. for 3 hours in a nitrogen atmosphere, thereby synthesizing an indium tin stearate compound, which is a precursor of indium-doped tin oxide (ITO) primary particles, and thermally decomposing this precursor. According to this method, ITO primary particles having a particle size of 7 nm or less without agglomeration are obtained without adding an organic solvent.

CITATION LIST

[Non-Patent Literature 1]
Shaojuan Luo, et al. "Synthesis and application of non-agglomerated ITO nanocrystals via pyrolysis of indium-tin stearate without using additional organic solvents", J Nanopart Res Vol. 16(8) 2014, 2561 pp 1-12

SUMMARY OF INVENTION

Technical Problem

It is believed that the stearic acid used in Non-Patent Literature 1 modifies the surface of the finally obtainable ITO primary particles and acts as a protective group.

However, since stearic acid is a fatty acid having a relatively long-chain with 18 carbon atoms, ITO primary particles wrapped with stearic acid as a protective group are likely to have wide grain spacing. For this reason, when an infrared-radiation-shielding film was produced using such ITO primary particles, there was a problem in that the infrared-radiation shielding effect was not sufficient.

An object of the present invention is to provide a method for producing a metal oxide dispersion liquid for forming a film having high infrared-radiation shielding performance and high transparency.

Solution to Problem

A first aspect of the present invention is a method for producing a dispersion liquid in which metal oxide secondary particles formed by metal oxide primary particles agglomerated together are dispersed in a hydrophobic solvent as a final dispersing solvent, the method including the following steps.

(a) A step of mixing, by a direct method or a metathesis method, a fatty acid of $C_nH_{2n}O_2$ (n=5 to 14) with each of metal sources including a plurality of kinds of metals selected from the group consisting of Zn, In, Sn, Sb, and Al, metal oxides of the metals, or metal hydroxides of the metals, and thereby obtaining a mixture of a plurality of kinds of fatty acid metal salts. The direct method is a method of causing a fatty acid to directly react with a metal compound, and the metathesis method is a method of saponifying a fatty acid with caustic soda, caustic potash, or the like to obtain an alkali soap, and then causing this to react with a metal compound.

(b) A step of heating the mixture of fatty acid metal salts at a temperature of 130° C. to 250° C., subsequently cooling the mixture, and thereby obtaining a metal soap, which is a precursor of the metal oxide primary particles.

(c) A step of heating the precursor of the metal oxide primary particles at a temperature of 200° C. to 350° C., and thereby dispersing the metal oxide primary particles in a melt of the precursor.

(d) A step of adding a washing solvent that has, when a polarization term of Hansen solubility parameter (HSP) of the solvent is designated as $\delta P$ (energy based on intermolecular dipole interaction/unit: $MPa^{0.5}$), a $\delta P$ value higher by 5 to 12 than the $\delta P$ value of the final dispersing solvent, to the metal oxide primary particles dispersed in the melt, thereby washing the metal oxide primary particles while simultaneously causing the metal oxide primary particles to agglomerate, and thereby obtaining metal oxide secondary particles in the washing solvent.

(e) A step of removing the washing solvent present in the dispersion liquid of the metal oxide secondary particles.

(f) A step of repeating the step (d) and step (e) once or twice or more.

(g) A step of adding, after the step (f), a hydrophobic solvent as the final dispersing solvent to the metal oxide secondary particles from which the washing solvent has been removed, and dispersing the metal oxide secondary particles having an average particle size of 50 nm to 150 nm in the hydrophobic solvent.

A second aspect of the present invention is an invention according to the first aspect and is a method for producing a metal oxide dispersion liquid, the method including, between the step (a) and the step (b), or between the step (b) and the step (c), a step of adding a high-boiling-point solvent to the mixture of fatty acid metal salts or to the precursor of the metal oxide primary particles.

A third aspect of the present invention is an invention according to the first aspect or the second aspect and is a method for producing a metal oxide dispersion liquid, wherein the metal oxide of the metal oxide primary particles and the metal oxide secondary particles is at least one kind of tin-doped indium oxide (ITO), antimony-doped tin oxide (ATO), antimony-doped zinc oxide (AZO), and aluminum-doped zinc oxide.

A fourth aspect of the present invention is a method for producing an infrared-radiation-shielding film by applying the dispersion liquid produced by the method according to any of the first to third aspects on a base material and thereby forming an infrared-radiation-shielding film.

Advantageous Effects of Invention

In the production method according to the first aspect of the present invention, a fatty acid of $C_nH_{2n}O_2$ (n=5 to 14) and a metal source including a plurality of kinds of metals selected from the group consisting of Zn, In, Sn, Sb, and Al, metal oxides, or metal hydroxides are mixed by a direct method or a metathesis method, thereby a plurality of kinds of fatty acid metal salts is obtained, subsequently the fatty acid metal salts are heated at a predetermined temperature and cooled, and thereby a metal soap, which is a precursor of metal oxide primary particles, is synthesized.

By heating this precursor at a predetermined temperature, the precursor is melted, and metal oxide primary particles are generated and dispersed in the melt. Here, since the surface of the metal oxide primary particles thus generated is modified with the fatty acid, and this fatty acid serves as a protective group, these metal oxide primary particles do not easily agglomerate. When these primary particles are washed with a washing solvent in this state, and then the washing solvent is removed, unreacted fatty acid molecules are removed, and decomposition products of the precursor remaining on the surface of the metal oxide primary particles are also removed. As a result, the metal oxide primary particles come into contact with one another and easily form metal oxide secondary particles. Subsequently, when a hydrophobic solvent as a final dispersing solvent is added, a transparent dispersion liquid in which metal oxide secondary particles having an average particle size of 50 nm to 150 nm are dispersed in this hydrophobic solvent is obtained. In this dispersion liquid, since the metal oxide secondary particles to be dispersed in the hydrophobic solvent include an organic component on the surface, the metal oxide secondary particles are stabilized and dispersed.

When a film is formed by applying the transparent dispersion liquid on a base material, a film having high transparency is obtained. Furthermore, since the fatty acid of the present invention is a fatty acid of $C_nH_{2n}O_2$ (n=5 to 14) and has a relatively short chain length, and the metal oxide secondary particles in the dispersion liquid are aligned at a shortened distance between those particles, the effect of surface plasmon is exhibited, and due to this effect, the film has a higher reflectance in the infrared wavelength region and has superior infrared-radiation shielding performance. Furthermore, when a metal soap that is a precursor of the metal oxide primary particles is produced by a direct method, sodium or potassium does not remain as impurities in the organic protective material covering the metal oxide primary particles obtained by this method, and therefore, the finally obtainable dispersion liquid becomes more stable for a long time period.

In the production method of the second aspect of the present invention, after a plurality of kinds of fatty acid metal salts is obtained, or after a mixture of fatty acid metal salts is obtained, a high-boiling-point solvent is added to these fatty acid metal salts or to the mixture of fatty acid metal salts, the resulting mixture is heated, and thereby a metal oxide having a uniform primary particle size can be obtained. Therefore, secondary particles of the metal oxide can be stably dispersed, and an effect of easily obtaining a transparent dispersion liquid, or the like is obtained.

In the production method of the third aspect of the present invention, by selecting the metal source from the group consisting of Zn, In, Sn, Sb, and Al, a dispersion liquid of metal oxide secondary particles of tin-doped indium oxide (ITO), antimony-doped tin oxide (ATO), antimony-doped zinc oxide (AZO), or aluminum-doped zinc oxide (AlZO) is obtained.

In an infrared-radiation-shielding film formed by the method of the fourth aspect of the present invention, since the dispersion liquid for forming the film is transparent, a film having high transparency is formed. Furthermore, since the fatty acid of the film-forming raw material is a fatty acid of $C_nH_{2n}O_2$ (n=5 to 14) and has a relatively short chain length, and the metal oxide secondary particles in the dispersion liquid are aligned at a shortened distance between those particles, the effect of the surface plasmon is exhibited, and due to this effect, the reflection in the infrared wavelength region becomes higher, while the infrared-radiation shielding performance is high.

BRIEF DESCRIPTION OF DRAWINGS

FIG. 1 is a flowchart showing a method for producing a dispersion liquid of a metal oxide, as an embodiment of the present invention.

DESCRIPTION OF EMBODIMENTS

Next, embodiments for carrying out the present invention will be described with reference to the drawings.

First Embodiment

A first embodiment is a method for producing a metal soap that is a precursor of metal oxide primary particles by a direct method.

[Fatty Acid of Starting Raw Material]

The fatty acid of the present embodiment is a fatty acid of $C_nH_{2n}O_2$ (n=5 to 14). Specifically, examples include pentanoic acid (n=5), hexanoic acid (n=6), 4-methylpentanoic acid (n=6), heptanoic acid (n=7), octanoic acid (n=8), octylic acid (n=8), nonanoic acid (n=9), decanoic acid (n=10), dodecanoic acid (n=12), and tetradecanoic acid (n=14). In a case in which the number of carbon atoms, n, is 4 or less, when the finally obtainable metal oxide secondary particles are produced into a dispersion liquid, the dispersion stability of the dispersion liquid becomes poor. When the number of carbon atoms, n, is more than 15, the metal oxide secondary particles wrapped with a fatty acid having a carbon number of more than 15 as a protective group have wide grain spacings, and in a case in which an infrared-radiation-shielding film is produced using such secondary particles, the infrared-radiation shielding effect is inferior. A preferred number of carbon atoms is n=6 to 10.

[Metal Source of Starting Raw Material]

The metal source of the present embodiment is a metal, a metal oxide, or a metal hydroxide, and any one kind only or two or more kinds thereof may be used. In the direct method of the first embodiment, since it is required to produce a metal soap by directly mixing and reacting the above-mentioned fatty acid and the metal source, the metal constituting this metal, metal oxide, or metal hydroxide is selected from the group consisting of Zn, In, Sn, Sb, and Al, where sodium and potassium are not included.

In order to form a film having high infrared-radiation shielding performance, regarding the metal element that constitutes the metal, metal oxide, or metal hydroxide, it is necessary to use a plurality of kinds, that is, two or more different kinds, of metal elements. It is also possible to use a mixture of three or more kinds; however, two kinds of different species are preferred. For example, in the case of two kinds of In and Sn, In:Sn is used at a mass ratio of 80 to 95:20 to 5. In the case of two kinds of Sb and Sn, Sb:Sn is used at a mass ratio of 85 to 98:15 to 2. In the case of two kinds of Zn and Sb, Zn:Sb is used at a mass ratio of 85 to 98:15 to 2. In the case of two kinds of Zn and Al, Zn:Al is used at a mass ratio of 90 to 98:10 to 2.

Meanwhile, in a case in which Al is selected as the metal source, production by the metathesis method of the second embodiment that will be described below is preferred, and it is preferable to configure not a form of metal Al but a form of a metal oxide such as $Al_2O_3$ or a metal hydroxide such as Al(OH)$_3$. In a case in which three or more kinds of the metal elements constituting the metal, metal oxide, or metal hydroxide are used, in the above-described combination example of two kinds, a portion of the mass ratio of the secondly abundant element may be replaced with a third or subsequent element.

[Synthesis of Mixture of Plurality of Kinds of Fatty Acid Metal Salts]

As shown in FIG. 1, in step (a), the fatty acid and a plurality of kinds of the metal sources are mixed, and a mixture of a plurality of kinds of fatty acid metal salts is synthesized. Regarding the mixing of the fatty acid and the metal sources, it is preferable that the metal sources be added to the fatty acid in a melted state, and the mixture be stirred and mixed. Regarding this mixing proportion, it is preferable that the metal sources be added at a proportion of 5% by mass to 40% by mass, and more preferably 10% by mass to 30% by mass, in terms of the metal components in the metal sources with respect to 100% by mass of the fatty acid. When the amount of the metal components is less than 5% by mass, there is a problem in that a large amount of unreacted fatty acid remains, or the like, and when the amount is more than 40% by mass, there is a problem in that a metal content that does not contribute to the reaction is generated as a by-product, or the like.

[Synthesis of Precursor of Metal Oxide Primary Particles]

In step (b), the mixture of a plurality of kinds of fatty acid metal salts is heated and then cooled, and thereby a metal soap that is a precursor of the metal oxide primary particles is synthesized. Before the heating of the mixture of fatty acid metal salts in this step (b), when a high-boiling-point solvent such as n-octyl ether, octadecene octylamine, or dodecylamine is added to the mixture of a plurality of kinds of fatty acid metal salts, and then the resulting mixture is heated, a metal oxide having a uniform primary particle size can be obtained. Therefore, it is preferable for reasons such as that secondary particles of the metal oxide can be stably dispersed, and a transparent dispersion liquid is easily obtained.

The mixture obtained by mixing the fatty acid and the metal sources is heated at a temperature of 130° C. to 250° C., and preferably 150° C. to 230° C., which is higher than or equal to the melting temperature of the fatty acid and lower than the decomposition temperature, in an inert gas atmosphere of nitrogen, argon gas, or the like in the case in which the metal sources are metals, and in an inert gas atmosphere of nitrogen, argon gas or the like or in an air atmosphere in the case in which the metal sources are substances other than metals, and the mixture is maintained for 1 hour to 5 hours at this temperature. When the temperature is lower than 130° C., since the fatty acid metal salts have insufficient fluidity and do not melt, and sufficient mixing of a plurality of kinds of metal sources does not occur, the metal soap that is the above-described precursor is not synthesized. When the temperature is higher than 250° C., the fatty acid in the mixture is decomposed, and the metal soap that is the above-described precursor is not synthesized. The heating time and the heat-holding time can be appropriately changed within the above-described range according to the type of the metal sources, the mixing proportion with the fatty acid, and the like. By performing heating as described above and cooling to room temperature, a metal soap that is a precursor of the metal oxide primary particles is synthesized.

[Dispersion of Metal Oxide Primary Particles in Melt]

In step (c), the precursor of the metal oxide primary particles thus obtained is heated at a temperature of 200° C. to 350° C., and preferably 230° C. to 310° C., which is equal to or higher than the melting temperature of the precursor and lower than the decomposition temperature, and the precursor is maintained for 0.5 hours to 8 hours at this temperature. The above-mentioned high-boiling-point solvent may be added before heating the metal oxide primary particles in step (c). When the temperature is lower than 200° C., the precursor does not melt, generation of particles does not occur, and metal oxide primary particles are not produced. When the temperature is higher than 350° C., decomposition and carbonization of the fatty acid occur simultaneously with decomposition of the precursor, and there is a problem in that the metal oxide primary particles are not produced or the like. The heating time and the heat-holding time can be appropriately changed within the above-described range according to the type of the precursor, the type of the metal sources, and the like. As a result of the above-mentioned heating, the metal oxide primary particles are obtained in a state of being dispersed in the melt.

These metal oxide primary particles are primary particles having an average particle size of 80 nm or less, and preferably 5 nm to 50 nm, and the particle surface is modified with an organic protective group. For this reason, the primary particles have a feature that the particles are less likely to agglomerate together. Examples of the metal oxide primary particles of the present embodiment include primary particles of metal oxides such as indium-doped tin oxide (ITO), antimony-doped tin oxide (ATO), antimony-doped zinc oxide (AZO), and aluminum-doped zinc oxide (AlZO).

[Washing of Metal Oxide Primary Particles and Formation of Metal Oxide Secondary Particles in Washing Solvent]

In step (d), the metal oxide primary particles thus obtained are washed with a washing solvent. A main feature of the present embodiment resides in this washing solvent. When the polarization term of the Hansen solubility parameter (HSP) of the solvent is designated as $\delta P$ (unit: $MPa^{0.5}$), the $\delta P$ value of this washing solvent is to be higher by 5 to 12 than the $\delta P$ value of the hydrophobic solvent, which is the final dispersing solvent that finally disperses the metal oxide secondary particles. The value is more preferably higher by 7 to 11. In a case in which the difference between the $\delta P$ value of the washing solvent and the $\delta P$ value of the final dispersing solvent is less than 5, at the time of washing with the washing solvent, the metal oxide primary particles and the metal oxide secondary particles are satisfactorily dispersed in the washing solvent, and the recovery rate of the metal oxide primary particles and the metal oxide secondary particles from the washing solvent is deteriorated. Furthermore, washing of the metal oxide primary particles cannot be sufficiently achieved, and the infrared reflectance of the film formed by this dispersion liquid decreases. When the difference between the $\delta P$ value of the washing solvent and the $\delta P$ value of the final dispersing solvent is more than 12, unreacted materials cannot be washed, and the unreacted materials agglomerate together with the metal oxide primary particles and are incorporated into the metal oxide secondary particles. Thereby, the dispersion stability of the metal oxide secondary particles in the final dispersing solvent is impaired, the secondary particles precipitate in a short period of time, or the dispersion liquid loses transparency, and thus, the dispersion liquid turns cloudy.

Examples of the washing solvent include 2-butanol, 1-butanol, hexanol, 2-propanol, ethylene glycol monoethyl ether, ethylene glycol monomethyl ether, ethanol, methoxyethanol, acetone, propylene glycol, diethylene glycol, methanol, and water. It is also acceptable to mix a plurality of solvents satisfying the conditions. The respective values of the Hansen solubility parameters δD, δP, and δH of these washing solvents are shown in the following Table 1. δD represents the energy originating from the intermolecular dispersive force, δH represents the energy originating from the intermolecular hydrogen bonding force, and the unit for both is $MPa^{0.5}$.

TABLE 1

|  |  | Hansen solubility parameter | | |
| --- | --- | --- | --- | --- |
|  |  | δD | δP | δH |
| Washing solvent | 2-Butanol | 15.8 | 5.7 | 14.5 |
|  | 1-Butanol | 16 | 5.7 | 15.8 |
|  | Hexanol | 15.9 | 5.8 | 12.5 |
|  | 2-Propanol | 15.8 | 6.1 | 16.4 |
|  | Ethylene glycol monoethyl ether | 15.9 | 7.2 | 14 |
|  | Ethylene glycol monomethyl ether | 16 | 8.2 | 15 |
|  | Ethanol | 15.8 | 8.8 | 19.4 |
|  | Methoxyethanol | 16 | 9 | 18.5 |
|  | Acetone | 15.5 | 10.4 | 7 |
|  | Propylene glycol | 16.8 | 10.4 | 21.3 |
|  | Diethylene glycol | 16.6 | 12 | 19 |
|  | Methanol | 14.7 | 12.3 | 22.3 |
|  | Water | 15.5 | 16 | 42.3 |
| Final dispersing solvent | Benzene | 18.4 | 0 | 2 |
|  | Cyclopropane | 17.3 | 0 | 0 |
|  | Cyclohexane | 16.8 | 0 | 0.2 |
|  | Octadecane | 16.4 | 0 | 0 |
|  | Hexadecane | 16.3 | 0 | 0 |
|  | n-Tetradecane | 16.2 | 0 | 0 |
|  | n-Pentane | 14.5 | 0 | 0 |
|  | n-Hexane | 14.9 | 0 | 0 |
|  | Cyclohexane | 17.2 | 1 | 2 |
|  | p-Xylene | 17.8 | 1 | 3.1 |
|  | Toluene | 1.8 | 1.4 | 2 |

Regarding the washing with the washing solvent, the metal oxide primary particles dispersed in the melt are retained in the same container or are transferred into another container, the washing solvent is added to this container, the particles are mixed and stirred using a mixer or the like or are subjected to ultrasonic vibration, and thereby the metal oxide primary particles are washed in the container. When these primary particles are washed with the washing solvent, unreacted fatty acid molecules are removed, and decomposition products of the precursor remaining on the surfaces of the metal oxide primary particles are also removed. As a result, the metal oxide primary particles come into contact with each other and agglomerate, and the resultant easily forms metal oxide secondary particles.

[Removal of Washing Solvent]

In step (e), the washing solvent is removed from the container in which the metal oxide primary particles have been washed. As a method for this removal, a decantation method or a centrifugal separation method, by which the supernatant in the container is removed, is available. It is not necessary to completely remove the washing solvent.

[Repetition of Washing of Metal Oxide Primary Particles Using Washing Solvent and Removal of Washing Solvent]

In step (f), washing of the metal oxide primary particles using the washing solvent of the above-described step (d) and removal of the washing solvent of the above-described step (e) are repeated once or twice or more, and preferably 2 to 5 times. By repeating the washing, unreacted fatty acid and decomposition products of the precursor remaining on the surfaces of the metal oxide primary particles are further removed.

[Addition of Hydrophobic Solvent as Final Dispersing Solvent and Production of Dispersion Liquid of Metal Oxide Secondary Particles]

In step (g), a hydrophobic solvent as a final dispersing solvent is added to the metal oxide secondary particles from which the washing solvent has been removed, the mixture is stirred and mixed with an ultrasonic homogenizer, and the metal oxide secondary particles are dispersed in the final dispersing solvent. Since the average particle size of the metal oxide primary particles described above is 80 nm or less, a dispersion liquid of metal oxide secondary particles having an average particle size of 50 nm to 150 nm is obtained. When the average particle size of the metal oxide secondary particles is less than 50 nm, in a case in which an infrared-radiation-shielding film is produced using these secondary particles, the effect of the particle surface plasmon is not sufficiently exhibited, and the infrared-radiation shielding effect is inferior. When the average particle size is more than 150 nm, the dispersion stability of the metal oxide secondary particles in the final dispersing solvent is impaired, the secondary particles precipitate in a short period of time, or the dispersion liquid loses transparency, and the dispersion liquid turns cloudy. A preferred average particle size of the secondary particles is 60 nm to 120 nm.

The hydrophobic solvent, which is the final dispersing solvent, has a δP value of the Hansen solubility parameter HSP that is lower by 5 to 12 than the δP value of the aforementioned washing solvent. Examples of this hydrophobic solvent include benzene, cyclopropane, cyclohexane, octadecane, hexadecane, n-tetradecane, n-pentane, n-hexane, cyclohexane, p-xylene, and toluene. The respective values of the Hansen solubility parameters δD, δP, and δH of these final dispersing solvents are shown in the above-described Table 1. The δP value of the final dispersing solvent is preferably 2.0 or less so that this solvent exhibits hydrophobicity more effectively by excluding the hydrophilicity of this solvent. Since the metal oxide secondary particles include an organic component together with the metal oxides, the particles are stably dispersed in the hydrophobic solvent that is the final dispersing solvent. It is preferable that the hydrophobic solvent be added and mixed according to the method of applying the dispersion liquid that will be described below, such that the metal oxide secondary particles are included in an amount of 5% by mass to 60% by mass with respect to 100% by mass of the hydrophobic solvent.

The average particle size of the metal oxide primary particles obtained in step (c) and the average particle size of the metal oxide secondary particles obtained in step (g) are determined by capturing images using a transmission electron microscope (JEOL, Ltd.: Model name: JEM-2010F) at a magnification ratio of 100,000 times, processing the obtained images with a software program (product name: Image J), measuring the particle sizes of 300 particles, and calculating the average of those particle sizes.

Second Embodiment

A second embodiment is a method for producing a metal soap, which is a precursor of metal oxide primary particles, by a metathesis method.

[Synthesis of Mixture of Plurality of Kinds of Fatty Acid Metal Salts]

Also in this method, as shown in FIG. 1, in step (a), an aqueous solution of a fatty acid alkali salt produced by mixing the fatty acid and an aqueous solution of alkalis such as sodium hydroxide and potassium hydroxide is obtained.

This aqueous solution of the fatty acid alkali salts is mixed with metal salts such as a hydrochlorides or nitrates of a plurality of kinds of metals, and a mixture of a plurality of kinds of fatty acid metal salts is synthesized. Regarding the mixing of the fatty acid alkali salts and the metal salts, it is preferable that an aqueous solution of the metal salts be added to an aqueous solution in which the fatty acid alkali salts are dissolved, and then the mixture be stirred and mixed. At this time, the mixture may be heated to 30° C. to 80° C. in order to completely dissolve the fatty acid alkali salts. Furthermore, regarding this mixing proportion, the aqueous solution of metal salts is added such that the proportion of the metal components in the metal salts is 5% by mass to 40% by mass, and more preferably 10% by mass to 30% by mass, with respect to 100% by mass of the fatty acid component in the aqueous solution of the fatty acid alkali salts. When the amount of the metal components is less than 5% by mass, there is a risk of having a problem in that a large amount of unreacted fatty acid may remain, and when the amount is more than 40% by mass, there is a risk of having a problem in that a metal content that does not contribute to the reaction may be generated as by-products.

The fatty acid metal salts thus obtained are washed in order to remove unreacted fatty acid alkali salts or a salt that forms a composite product. As a washing method, a method of adding a large amount of water, stirring the mixture, subsequently performing filtration and drying, or the like is preferable. Step (b) to step (g) after step (a) are carried out in the same manner as in the first embodiment, and thereby a dispersion liquid of metal oxide secondary particles is obtained.

(Formation of Infrared-Radiation-Shielding Film)

The dispersion liquid of the metal oxide secondary particles obtained in step (g) of the first and second embodiments is applied on, for example, the surface of a transparent glass substrate or a resin film as a base material, dried at a predetermined temperature, and then subjected to a heating treatment, and thereby an infrared-radiation-shielding film having a film thickness of 0.1 μm to 2.0 μm, and more preferably 0.2 μm to 1.5 μm, is formed on the surface of the glass substrate or the surface of the resin film.

In a case in which the base material is a transparent glass substrate, for example, the heating treatment is carried out by maintaining the base material in an oxidizing atmosphere at a temperature of 50° C. to 250° C. for 5 minutes to 60 minutes. This temperature and this holding time are determined according to the adhesion strength required from the film. In a case in which the base material is a transparent resin film, for example, the heating treatment is carried out by maintaining the base material in an oxidizing atmosphere at a temperature of 40° C. to 130° C. for 5 minutes to 120 minutes. This temperature and this holding time are determined according to the adhesion strength required from the film and the heat resistance of the backing film.

EXAMPLE

Next, Examples of the present invention will be described in detail together with Comparative Examples.

Example 1

A metal soap that was a precursor of ITO primary particles was obtained by a direct method. Specifically, in a first container, octanoic acid as a fatty acid, and metal In and metal Sn as metal sources were weighed and mixed such that the metal components were incorporated at a mass ratio of In:Sn=95:5, and a mixture of fatty acid-In and fatty acid-Sn was obtained. The metal sources were added to the fatty acid at a proportion of 25% by mass in terms of metal component. In the first container, this mixture was heated to 210° C. in a nitrogen atmosphere and was maintained for 3 hours while being stirred. Thereafter, the mixture was cooled to room temperature, and thereby a metal soap as a precursor of ITO primary particles was obtained.

Subsequently, in the first container, the precursor of the ITO primary particles was heated to 270° C. and was further maintained for 3 hours while being stirred. As a result of heating, the ITO primary particles having the particle surface modified with an organic protective group were dispersed in the melt. Thereafter, a portion of the dispersion liquid cooled to room temperature was diluted, and the average particle size of the ITO primary particles was measured using the above-mentioned transmission electron microscope. The average particle size was 8 nm.

The dispersed ITO primary particles were transferred from the first container to a second container, ethanol (δP value of the polarization term of the Hansen solubility parameter HSP: 8.8) was added thereto as a washing solvent, and thereby the ITO primary particles were washed. The ITO primary particles that had begun to agglomerate were settled by a centrifugal separator, this was repeated three times, and thereby the primary particles agglomerated to form ITO secondary particles.

Ethanol was sufficiently removed from the second container containing the ITO secondary particles, toluene (δP value of the polarization term of the Hansen solubility parameter HSP: 1.4) was added to this second container as a final dispersing solvent, the ITO secondary particles were dispersed in the liquid to which this toluene had been added using an ultrasonic homogenizer, and thus a dispersion liquid of ITO secondary particles was obtained. The difference in the δP value of the HSP between methanol and toluene was 7.4. The average particle size of the ITO secondary particles in the dispersion liquid was measured using the above-mentioned transmission electron microscope, and the average particle size was 70 nm. The matters until this dispersion liquid of ITO secondary particles was obtained, the average primary particle size, and the average secondary particle size are shown in Table 2.

Examples 2 to 14, 17, and 19 and Comparative Examples 1 to 7 and 9 to 13

In Examples 2 to 14, 17, and 19 and Comparative Examples 1 to 7 and 9 to 13, metal soaps, which are precursors of metal oxide primary particles, were obtained by a direct method. As the fatty acids and metal sources as the starting raw materials of these, the kinds shown in the following Table 2 and Table 3 were selected, and the metal oxide primary particles shown in Table 2 and Table 3 were produced in the same manner as in Example 1, at the heating temperatures shown in Table 2 and Table 3.

Subsequently, in Examples 2 to 14, 17, and 19 and Comparative Examples 1 to 5 and 9 to 12, metal oxide secondary particles were obtained in the same manner as in Example 1, by washing the metal oxide primary particles for the same number of times as in Example 1 using the washing solvents shown in Table 4 and Table 5, and finally adding the final dispersing solvent shown in Table 4 and Table 5 thereto.

Meanwhile, as will be described later, in Comparative Examples 6, 7, and 13, since the precursor of the metal oxide primary particles and the metal oxide primary particles could not be produced, washing and various comparison tests that will be described later were not performed. The average primary particle size and the average secondary particle size of the metal oxide particles are shown in Table 2 and Table 3, and the δP value of the HSP of the washing solvent, the δP value of the HSP of the final dispersing solvent, and the difference between the two are shown in Table 4 and Table 5.

TABLE 2

| | Production method for metal soap | Fatty acid Type | Carbon number | Metal source Type | Mass ratio | Type | Mass ratio | Metal oxide particles Type | Average primary particle size (nm) | Average secondary particle size (nm) | Heating temperature for mixture (° C.) | Heating temperature for precursor (° C.) |
|---|---|---|---|---|---|---|---|---|---|---|---|---|
| Example 1 | Direct method | Octanoic acid | 8 | Metal In | 95 | Metal Sn | 5 | ITO | 8 | 70 | 210 | 270 |
| Example 2 | Direct method | Decanoic acid | 10 | Metal In | 90 | Metal Sn | 10 | ITO | 10 | 50 | 230 | 260 |
| Example 3 | Direct method | Nonanoic acid | 9 | $In_2O_3$ | 95 | $SnO_2$ | 5 | ITO | 20 | 100 | 210 | 265 |
| Example 4 | Direct method | 4-Methylpentanoic acid | 6 | In hydroxide | 85 | Sn hydroxide | 15 | ITO | 20 | 90 | 170 | 250 |
| Example 5 | Direct method | Hexanoic acid | 6 | In hydroxide | 90 | Sn hydroxide | 10 | ITO | 25 | 100 | 140 | 250 |
| Example 6 | Direct method | Tetradecanoic acid | 14 | $In_2O_3$ | 90 | $SnO_2$ | 10 | ITO | 10 | 80 | 250 | 290 |
| Example 7 | Direct method | Octylic acid | 8 | Metal In | 90 | Metal Sn | 10 | ITO | 20 | 120 | 230 | 280 |
| Example 8 | Direct method | Decanoic acid | 10 | Metal In | 95 | Metal Sn | 5 | ITO | 30 | 110 | 230 | 260 |
| Example 9 | Direct method | Heptanoic acid | 7 | $In_2O_3$ | 93 | $SnO_2$ | 7 | ITO | 10 | 60 | 160 | 255 |
| Example 10 | Direct method | Pentanoic acid | 5 | Metal In | 90 | Metal Sn | 10 | ITO | 25 | 70 | 130 | 200 |
| Example 11 | Direct method | Nonanoic acid | 9 | Sn hydroxide | 95 | Sb hydroxide | 5 | ATO | 30 | 100 | 180 | 260 |
| Example 12 | Direct method | Hexanoic acid | 6 | $In_2O_3$ | 95 | $SnO_2$ | 5 | ITO | 20 | 90 | 170 | 250 |
| Example 13 | Direct method | Decanoic acid | 10 | Zn hydroxide | 95 | Metal Sb | 5 | AZO | 30 | 100 | 160 | 240 |
| Example 14 | Direct method | Nonanoic acid | 9 | Metal In | 92 | Metal Sn | 8 | ITO | 25 | 100 | 190 | 300 |
| Example 15 | Metathesis method | Decanoic acid | 10 | In chloride | 95 | Sn chloride | 5 | ITO | 8 | 80 | 150 | 260 |
| Example 16 | Metathesis method | Decanoic acid | 10 | In chloride | 90 | Sn chloride | 10 | ITO | 10 | 100 | 170 | 290 |
| Example 17 | Direct method | Nonanoic acid | 9 | $IniO3$ | 95 | $SnO_2$ | 5 | ITO | 15 | 110 | 210 | 260 |
| Example 18 | Metathesis method | Decanoic acid | 10 | Zn chloride | 98 | Al chloride | 2 | AlZO | 20 | 80 | 230 | 290 |
| Example 19 | Direct method | Nonanoic acid | 9 | Metal In | 95 | Metal Sn | 5 | ITO | 20 | 100 | 210 | 350 |

TABLE 3

| | Production method for metal soap | Fatty acid Type | Carbon number | Metal source Type | Mass ratio | Type | Mass ratio | Metal oxide particles Type | Average primary particle size (nm) | Average secondary particle size (nm) | Heating temperature for mixture (° C.) | Heating temperature for precursor (° C.) |
|---|---|---|---|---|---|---|---|---|---|---|---|---|
| Comparative Example 1 | Direct method | Octanoic acid | 8 | Metal In | 90 | Metal Sn | 10 | ITO | 10 | 80 | 200 | 280 |
| Comparative Example 2 | Direct method | Decanoic acid | 10 | In hydroxide | 90 | Sn hydroxide | 10 | ITO | 15 | 220 | 220 | 310 |
| Comparative Example 3 | Direct method | Heptanoic acid | 7 | In hydroxide | 90 | Sn hydroxide | 10 | ITO | 10 | 70 | 180 | 265 |
| Comparative Example 4 | Direct method | Decanoic acid | 10 | $In_2O_3$ | 95 | $SnO_2$ | 5 | ITO | 30 | 300 | 230 | 260 |
| Comparative Example 5 | Direct method | Nonanoic acid | 9 | Sn hydroxide | 95 | Sb hydroxide | 5 | ATO | 5 | 20 | 160 | 260 |
| Comparative Example 6 | Direct method | Hexanoic acid | 6 | Metal In | 90 | Metal Sn | 10 | ITO | 5 | 50 | 150 | 150 |

TABLE 3-continued

| | Production method for metal soap | Fatty acid Type | Carbon number | Metal source Type | Mass ratio | Type | Mass ratio | Metal oxide particles Type | Average primary particle size (nm) | Average secondary particle size (nm) | Heating temperature for mixture (° C.) | Heating temperature for precursor (° C.) |
|---|---|---|---|---|---|---|---|---|---|---|---|---|
| Comparative Example 7 | Direct method | Octanoic acid | 8 | Metal In | 95 | Metal Sn | 5 | ITO | 8 | 70 | 280 | — |
| Comparative Example 8 | Metathesis method | Nonanoic acid | 9 | In chloride | 95 | Sn chloride | 5 | ITO | 20 | 100 | 210 | 370 |
| Comparative Example 9 | Direct method | Octanoic acid | 8 | Metal In | 90 | Metal Sn | 10 | ITO | 10 | 80 | 240 | 290 |
| Comparative Example 10 | Direct method | Decanoic acid | 10 | $In_2O_3$ | 95 | $SnO_2$ | 5 | ITO | 10 | 100 | 240 | 260 |
| Comparative Example 11 | Direct method | Stearic acid | 18 | Metal In | 90 | Metal Sn | 10 | ITO | 30 | 120 | 240 | 310 |
| Comparative Example 12 | Direct method | Propionic acid | 3 | Sn hydroxide | 90 | In hydroxide | 10 | ITO | 10 | 30 | 130 | 200 |
| Comparative Example 13 | Direct method | Nonanoic acid | 9 | Sn hydroxide | 95 | Sb hydroxide | 5 | ATO | 5 | 70 | 80 | — |

TABLE 4

| | Washing solvent Type | δP value of HSP | Final dispersing solvent Type | δP value of HSP | Difference of δP values of HSP | Long-term stability of dispersion liquid | Evaluation of film Maximum infrared reflectance (%) | Transparency |
|---|---|---|---|---|---|---|---|---|
| Example 1 | Ethanol | 8.8 | Toluene | 1.4 | 7.4 | Excellent | 40 | Good |
| Example 2 | 2-Propanol | 6.1 | p-Xylene | 1 | 5.1 | Good | 61 | Good |
| Example 3 | Methanol | 12.3 | Toluene | 1.4 | 10.9 | Excellent | 38 | Good |
| Example 4 | Methoxyethanol | 9 | n-Hexane | 0 | 9 | Good | 46 | Good |
| Example 5 | Ethanol | 8.8 | Benzene | 0 | 8.8 | Excellent | 51 | Good |
| Example 6 | 2-Propanol | 6.1 | n-Pentane | 0 | 6.1 | Excellent | 59 | Good |
| Example 7 | Ethanol | 8.8 | Toluene | 1.4 | 7.4 | Good | 55 | Acceptable |
| Example 8 | 2-Propanol | 6.1 | Octadecane | 0 | 6.1 | Good | 43 | Good |
| Example 9 | Ethylene glycol monomethyl ether | 8.2 | p-Xylene | 1 | 7.2 | Good | 35 | Good |
| Example 10 | Methanol | 12.3 | Toluene | 1.4 | 10.9 | Excellent | 47 | Good |
| Example 11 | Acetone | 10.4 | Toluene | 1.4 | 9 | Excellent | 35 | Acceptable |
| Example 12 | Diethylene glycol | 12 | n-Pentane | 0 | 12 | Excellent | 53 | Acceptable |
| Example 13 | Ethanol | 8.8 | Toluene | 1.4 | 7.4 | Good | 63 | Good |
| Example 14 | Methanol | 12.3 | p-Xylene | 1 | 11.3 | Good | 65 | Good |
| Example 15 | Ethanol | 8.8 | Toluene | 1.4 | 7.4 | Good | 52 | Good |
| Example 16 | Methoxyethanol | 9 | n-Hexane | 0 | 9 | Excellent | 60 | Good |
| Example 17 | Ethanol | 8.8 | Benzene | 0 | 8.8 | Excellent | 48 | Good |
| Example 18 | Methanol | 12.3 | Toluene | 1.4 | 10.9 | Excellent | 37 | Acceptable |
| Example 19 | Ethanol | 8.8 | Toluene | 1.4 | 7.4 | Excellent | 41 | Acceptable |

TABLE 5

| | Washing solvent | | Final dispersing solvent | | Difference of δP values of HSP | Long-term stability of dispersion liquid | Evaluation of film | |
|---|---|---|---|---|---|---|---|---|
| | Type | δP value of HSP | Type | δP value of HSP | | | Maximum infrared reflectance (%) | Transparency |
| Comparative Example 1 | 2-Butanol | 5.7 | Toluene | 1.4 | 4.3 | Poor | 26 | Acceptable |
| Comparative Example 2 | Water | 16 | Toluene | 1.4 | 14.6 | Poor | 34 | Poor |
| Comparative Example 3 | Hexanol | 5.8 | p-Xylene | 1 | 4.8 | Poor | 19 | Acceptable |
| Comparative Example 4 | Ethanol | 8.8 | 2-Butanol | 5.7 | 3.1 | Poor | 17 | Poor |
| Comparative Example 5 | Hexanol | 5.8 | p-Xylene | 1 | 4.8 | Poor | 20 | Poor |
| Comparative Example 6 | — | — | — | — | — | — | — | — |
| Comparative Example 7 | — | — | — | — | — | — | — | — |
| Comparative Example 8 | — | — | — | — | — | — | — | — |
| Comparative Example 9 | 2-Butanol | 5.7 | Toluene | 1.4 | 4.3 | Poor | 26 | Poor |
| Comparative Example 10 | Water | 16 | Toluene | 1.4 | 14.6 | Poor | 22 | Poor |
| Comparative Example 11 | Ethanol | 8.8 | Toluene | 1.4 | 7.4 | Poor | 21 | Poor |
| Comparative Example 12 | Ethanol | 8.8 | Toluene | 1.4 | 7.4 | Poor | 16 | Acceptable |
| Comparative Example 13 | — | — | — | — | — | — | — | — |

Example 15

(Production of Precursor of Metal Oxide Primary Particles)

A metal soap that is a precursor of ITO primary particles was obtained by a metathesis method. Specifically, an aqueous solution of sodium decanoate obtained by mixing decanoic acid as a fatty acid and an aqueous solution of sodium hydroxide, and an aqueous solution of indium chloride as a metal source were mixed in a state of being heated to 50° C., and thereby a first mixture of decanoic acid and indium chloride was obtained. On the other hand, the aqueous solution of sodium decanoate and an aqueous solution of tin chloride as a metal source were mixed in a state of being heated to 50° C., and thereby a second mixture of decanoic acid and tin chloride was obtained. In the first container, the first mixture and the second mixture were weighed, added, and mixed such that the metal components were incorporated at a mass ratio of In:Sn=95:5, and a mixture of fatty acid-indium and fatty acid-tin was obtained. The metal sources were added to the fatty acid at a proportion of 25% by mass in terms of metal component. In the first container, the mixture of fatty acid-indium and fatty acid-tin was heated to 150° C. in a nitrogen atmosphere and was maintained for 2 hours while being stirred. Thereafter, the mixture was cooled to room temperature, and thereby a metal soap as a precursor of ITO primary particles was obtained.

Examples 16 and 18 and Comparative Example 8

(Production of Precursor of Metal Oxide Primary Particles)

In Examples 16 and 18 and Comparative Example 8, as the fatty acids and metal sources as the starting raw materials of these, the kinds shown in the above-described Table 2 and Table 3 were selected, and the metal oxide primary particles shown in Table 2 and Table 3 were produced by a metathesis method in the same manner as in Example 15, at the heating temperatures shown in Tables 2 and 3.

Examples 15, 16, and 18 and Comparative Example 8

(Production of Metal Oxide Secondary Particles)

Subsequently, in Examples 15, 16, and 18, metal oxide secondary particles were obtained in the same manner as in Example 1 by washing the obtained metal oxide primary particles for the same number of times as in Example 1 using the washing solvents shown in Table 4 and Table 5, and finally adding the final dispersing solvents shown in Table 4 and Table 5 thereto.

On the other hand, in Comparative Example 8, as will be described below, since metal oxide primary particles could not be produced, washing and various comparison tests that will be described later were not performed. The average primary particle size and the average secondary particle size of the metal oxide particles are shown in Table 2 and Table 3, and the δP value of the HSP of the washing solvent, the δP value of the HSP of the final dispersing solvent, and the difference between the two are shown in Table 4 and Table 5.

(Metal Sources in Each Example and Each Comparative Example)

In Examples 2, 7, 8, 10, 14, and 19 and Comparative Examples 1, 6, 7, 9, and 11, dispersion liquids of ITO secondary particles were obtained using metal In and metal Sn as the same metal source as in Example 1. In Examples 3, 6, 9, 12, and 17 and Comparative Examples 4 and 10, dispersion liquids of ITO secondary particles were obtained using $In_2O_3$ and $SnO_2$ as the metal sources. In Examples 4 and 5 and Comparative Examples 2, 3, and 12, dispersion liquids of ITO secondary particles were obtained using In hydroxide and Sn hydroxide as the metal sources. In Example 11 and Comparative Examples 5 and 13, dispersion liquids of ATO secondary particles were obtained using Sn hydroxide and Sb hydroxide as the metal sources. In Example 13, a dispersion liquid of AZO secondary particles was obtained using Zn hydroxide and metal Sb as the metal sources. In Examples 15 and 16 and Comparative Example 8, dispersion liquids of ITO secondary particles were obtained using In chloride and Sn chloride as the metal sources. In Example 18, a dispersion liquid of AlZO secondary particles was obtained using Zn chloride and Al chloride as the metal sources.

<Comparison Test and Evaluation>

The long-term stability of 32 kinds of the dispersion liquids of metal oxide secondary particles obtained in Examples 1 to 19 and Comparative Examples 1 to 13, the maximum infrared reflectance (%) of films formed by applying these dispersion liquids on base materials, and the transparency of the films were evaluated by the following methods. These results are presented in Table 4 and Table 5.

(1) Long-Term Stability of Dispersion Liquid

The 32 kinds of the dispersion liquids of metal oxide secondary particles were each separately sealed in glass bottles and were left to stand still in an environment at a temperature of 25° C. and a relative humidity of 50%, and the color of the liquids in the form of solution was checked after one month and after three months. A case in which the color of the liquid was the same color throughout and no clear liquid was recognized in the supernatant until 3 months later was regarded as "excellent"; a case in which there was no change until 1 month later, but a clear liquid was recognized in the supernatant of the liquid at a time point around 3 months was regarded as "good"; and a case in which a clear liquid was recognized in the supernatant of the liquid at a time point after 1 month was regarded as "poor".

(2) Maximum Reflectance of Film for Infrared-Radiation

The 32 kinds of dispersion liquids were each separately supplied onto the surface of a transparent soda lime glass substrate having a size of 50 mm×50 mm and a thickness of 0.7 mm, spin-coating was performed at a rotation speed of 500 rpm for 60 seconds, and thereby a coating film was formed. Furthermore, an epoxy-based resin coating agent (GLASSCA, manufactured by JSR Corporation, product name: GLASSCA) was supplied onto the above-mentioned coating film, the coating agent was spin-coated at a rotation speed of 2,000 rpm for 60 seconds, subsequently this film was dried at 120° C. for 20 minutes, and thereby 32 kinds of films each having a 0.3 μm-thick metal oxide secondary particle-containing layer and a 2 μm-thick overcoat layer were formed. For these films, the maximum reflectance in the wavelength region of 800 to 2,500 nm was measured using a spectrophotometer (manufactured by Hitachi High-Technologies Corporation, product name: Model U-4100).

(3) Transparency of Film

The transparency of the 32 kinds of films was evaluated using the transmittance of the films. The transmittance of each film for visible light having a wavelength of 450 nm was measured using a spectrophotometer (U-4100 manufactured by Hitachi High-Technologies Corporation) according to the standards (JIS R 3216-1998). In the evaluation of the visible light transmittance, a case in which the transmittance of the film-attached glass at a wavelength of 450 nm was 85% or higher was regarded as "good"; a case in which the transmittance was 80% or higher and lower than 85% was regarded as "acceptable"; and a case in which the transmittance was lower than 80% was regarded as "poor".

As is obvious from Table 4 and Table 5, in Comparative Example 1, since the difference between the δP value of the HSP of the washing solvent and the δP value of the HSP of the dispersing solvent was 4.3 and too small, the effect of washing the ITO primary particles was not sufficient, and therefore, the effect of the particle surface plasmon in the formed film was not sufficiently exhibited, while the maximum infrared reflectance of the film was as low as 26%.

In Comparative Example 2, since the difference between the δP value of the HSP of the washing solvent and the δP value of the HSP of the dispersing solvent was 14.6 and too large, the average particle size of the ITO secondary particles was increased, and the dispersion stability of the ITO secondary particles in the final dispersing solvent was impaired, so that the dispersion liquid became cloudy. For this reason, the long-term stability of the dispersion liquid and the transparency of the film were both poor.

In Comparative Example 3, since the difference between the δP value of the HSP of the washing solvent and the δP value of the HSP of the dispersing solvent was 4.8 and too small, the effect of washing the ITO primary particles was not sufficient, and therefore, the effect of the particle surface plasmon in the formed film was not sufficiently exhibited, while the maximum infrared reflectance of the formed film was as low as 19%.

In Comparative Example 4, since the difference between the δP value of the HSP of the washing solvent and the δP value of the HSP of the dispersing solvent was 3.1 and too small, the effect of washing the ITO primary particles was not sufficient, and the recovery rates for the ITO primary particles and the ITO secondary particles from the washing solvent were deteriorated. Furthermore, since the average particle size of the ITO secondary particles was 300 nm and too large, the long-term stability of the dispersion liquid and the transparency of the film were both poor.

In Comparative Example 5, since the difference between the δP value of the HSP of the washing solvent and the δP value of the HSP of the dispersing solvent was 4.8 and too small, the effect of washing the ATO primary particles was not sufficient, and the recovery rates for the ATO primary particles and the ATO secondary particles from the washing solvent were deteriorated. Furthermore, since the average particle size of the ATO secondary particles was 20 nm and too small, the maximum infrared reflectance of the formed film was as low as 20%, and the long-term stability of the dispersion liquid and the transparency of the film were poor.

In Comparative Example 6, since the heating temperature for the precursor was 150° C. and too low, it was not possible to produce ITO primary particles. In Comparative Example 7, since the heating temperature for the mixture was 280° C. and too high, the fatty acid in the mixture was decomposed, and a metal soap as a precursor of ITO primary particles could not be obtained. In Comparative Example 8, since the heating temperature for the precursor was 370° C. and too high, decomposition and carbonization of the fatty acid occurred simultaneously with decomposition of the precursor of ITO primary particles, and the ITO primary particles could not be obtained.

In Comparative Example 9, since the difference between the δP value of the HSP of the washing solvent and the δP value of the HSP of the dispersing solvent was 4.3 and too small, the effect of washing the ITO primary particles was not sufficient, and the interparticle distance became indeterminate. For this reason, the maximum infrared reflectance of the film was as low as 26%.

In Comparative Example 10, since the difference between the δP value of the HSP of the washing solvent and the δP value of the HSP of the dispersing solvent was 14.6 and too large, the dispersion stability of the ITO secondary particles in the final dispersing solvent was impaired, and the dispersion liquid became cloudy. For this reason, the long-term stability of the dispersion liquid and the transparency of the film were both poor.

In Comparative Example 11, since the chain length of the fatty acid used as the raw material was too long, the interparticle distance of the ITO particles thus obtained was indeterminate. For this reason, the reflectance of the obtained film was as low as 21%. The long-term stability of the dispersion liquid and the transparency of the film were both poor.

In Comparative Example 12, since the chain length of the fatty acid used as a raw material was too short, the grain spacing of the ITO particles thus obtained was indeterminate. For this reason, the reflectance of the obtained film was as low as 16%. In addition, the long-term stability of the dispersion liquid was poor. In Comparative Example 13, since the heating temperature for the mixture was 80° C. and too low, a metal soap as a precursor of ATO primary particles could not be obtained.

In contrast, in the dispersion liquids of metal oxide secondary particles of Examples 1 to 19, which had been produced using fatty acids having 5 to 14 carbon atoms under the necessary conditions described in the first aspect, by heating the mixture at a predetermined temperature, and heating the precursor at a predetermined temperature, and in which the difference between the δP value of the HSP of the washing solvent and the δP value of the HSP of the dispersing solvent was in the range of 5 to 12, the long-term stability of the dispersion liquids was "good" or "excellent". Furthermore, the maximum infrared reflectance of the films produced from these dispersion liquids was 35% to 65%, and the infrared-radiation shielding performance was excellent. Moreover, the transparency of these dispersion liquids of the metal oxide secondary particles was "acceptable" or "good".

INDUSTRIAL APPLICABILITY

A dispersion liquid of metal oxide secondary particles produced by the method of the present invention is such that when this is applied on a transparent base material such as a glass plate or a film, and thereby an infrared-radiation-shielding film is formed, a transparent infrared-radiation-shielding film having high infrared-radiation shielding performance can be obtained. Therefore, industrial utilization thereof is possible.

What is claimed is:

1. A method for producing a dispersion liquid in which metal oxide secondary particles formed by metal oxide primary particles agglomerated together are dispersed in a hydrophobic solvent as a final dispersing solvent, the method comprising:
   (a) a step of mixing, by a direct method or a metathesis method, a fatty acid of $C_nH_{2n}O_2$ (n=5 to 14) with each of metal sources including a plurality of kinds of metals selected from the group consisting of Zn, In, Sn, Sb, and Al, metal oxides of the metals, metal hydroxides of the metals, and thereby obtaining a mixture of a plurality of kinds of fatty acid metal salts;
   (b) a step of heating the mixture of fatty acid metal salts at a temperature of 130° C. to 250° C., subsequently cooling the mixture, and thereby obtaining a metal soap, which is a precursor of the metal oxide primary particles;
   (c) a step of heating the precursor of the metal oxide primary particles at a temperature of 200° C. to 350° C., and thereby dispersing the metal oxide primary particles in a melt of the precursor;
   (d) a step of adding a washing solvent that has, when a polarization term of Hansen solubility parameter (HSP) of the solvent is designated as δP, a δP value higher by 5 to 12 than the δP value of the final dispersing solvent, to the metal oxide primary particles dispersed in the melt, thereby washing the metal oxide primary particles while simultaneously causing the metal oxide primary particles to agglomerate, and thereby obtaining metal oxide secondary particles in the washing solvent;
   (e) a step of removing the washing solvent present in the dispersion liquid of the metal oxide secondary particles;
   (f) a step of repeating the step (d) and step (e) once or twice or more; and
   (g) a step of adding, after the step (f), a hydrophobic solvent as the final dispersing solvent to the metal oxide secondary particles from which the washing solvent has been removed, and dispersing the metal oxide secondary particles having an average particle size of 50 nm to 150 nm in the hydrophobic solvent.

2. The production method according to claim 1, wherein between the step (a) and the step (b), or between the step (b) and the step (c), a high-boiling-point solvent is added to the mixture of fatty acid metal salts or to the precursor of the metal oxide primary particles.

3. The production method according to claim 1, wherein the metal oxide of the metal oxide primary particles and the metal oxide secondary particles is at least one kind of tin-doped indium oxide (ITO), antimony-doped tin oxide (ATO), antimony-doped zinc oxide (AZO), and aluminum-doped zinc oxide (AlZO).

4. The method for producing an infrared-radiation shielding-film by applying the dispersion liquid produced by the method according to claim 1 on a base material and thereby forming an infrared-radiation-shielding film.

5. The production method according to claim 2, wherein the metal oxide of the metal oxide primary particles and the metal oxide secondary particles is at least one kind of tin-doped indium oxide (ITO), antimony-doped tin oxide (ATO), antimony-doped zinc oxide (AZO), and aluminum-doped zinc oxide (AlZO).

6. The method for producing an infrared-radiation shielding-film by applying the dispersion liquid produced by the method according to claim 2 on a base material and thereby forming an infrared-radiation-shielding film.

7. The method for producing an infrared-radiation shielding-film by applying the dispersion liquid produced by the method according to claim 3 on a base material and thereby forming an infrared-radiation-shielding film.

8. The method for producing an infrared-radiation shielding-film by applying the dispersion liquid produced by the method according to claim 5 on a base material and thereby forming an infrared-radiation-shielding film.

* * * * *